(12) United States Patent
DeFazio

(10) Patent No.: US 7,144,124 B2
(45) Date of Patent: Dec. 5, 2006

(54) FOOT REFLECTOR ... FOR YOUR HEALTH

(76) Inventor: Frances DeFazio, 101 Harrison Ave., North Plainfield, NJ (US) 07060

( * ) Notice: Subject to any disclaimer, the term of this patent is extended or adjusted under 35 U.S.C. 154(b) by 88 days.

(21) Appl. No.: 11/117,628

(22) Filed: Apr. 29, 2005

(65) Prior Publication Data

US 2006/0245091 A1 Nov. 2, 2006

(51) Int. Cl.
*G02B 5/08* (2006.01)
*A61B 1/00* (2006.01)

(52) U.S. Cl. .................. 359/865; 359/857; 600/247; 600/592

(58) Field of Classification Search ........... 359/850, 359/857, 860, 862, 863, 865, 882; 600/247, 600/248, 592
See application file for complete search history.

(56) References Cited

U.S. PATENT DOCUMENTS

| | | | | |
|---|---|---|---|---|
| 1,643,626 A | * | 9/1927 | May ..................... | 359/857 |
| 2,136,832 A | * | 11/1938 | Weisberger .............. | 600/248 |
| 2,480,361 A | * | 8/1949 | Doumitt ................. | 600/592 |
| 4,534,365 A | * | 8/1985 | Bonetta et al. .......... | 600/592 |
| 6,053,618 A | * | 4/2000 | Arpin ................... | 359/872 |
| 6,598,992 B1 | * | 7/2003 | Ames .................... | 362/138 |

* cited by examiner

*Primary Examiner*—Mark A. Robinson

(57) ABSTRACT

The Foot Reflector ... for Your Health is a unique combination of three normally reflective mirrors, two magnification mirrors, and a leg support. The items are all attached to a structure, which allows the user to comfortably self-examine the entire area of the foot. This includes the toes and the area between them. The simplicity of the design, the low cost of manufacture, the ease of maintenance and use make it a device that could be readily available to anyone with a circulatory problem. The fact that four of the mirrors can be adjusted so that no part of the foot is missed during self-examination is unique to the Foot Reflector ... for Your Health.

6 Claims, 9 Drawing Sheets

"THE FOOT REFLECTOR... FOR YOUR HEALTH"
A perspective view of the entire unit.

"THE FOOT REFLECTOR... FOR YOUR HEALTH"
A perspective view of the leg support with broken lines superimposed.

"FOOT REFLECTOR... FOR YOUR HEALTH"
A perspective view of the entire unit from the back showing the round magnified mirrors at the rear of mirrors 2 and 3.

FOOT REFLECTOR ... FOR YOUR HEALTH

BACKGROUND OF THE INVENTION

1. TECHNICAL FIELD

The purpose of this invention is to help older people and those who were infirm, obese, or have diabetes to be able to self-examine their entire foot.

This invention will help in the early detection of infection or foreign objects located anywhere on the foot.

Many diabetics have problems with circulation in their feet, and they therefore cannot feel an infection or foreign object in their feet.

Many people do not have someone to examine their feet.

Many people do not want others looking at their feet.

Many older or diabetic people have weak vision and need the help of magnification while self-examining their feet.

BRIEF SUMMARY OF THE INVENTION

Presently there is not readily available any simply to operate reflective device for the entire foot self-examination process. This is a simple and low cost reflective device, which allows all users to self-examine their entire foot area for infections and foreign objects. In accordance with one preferred aspect of the invention, there is provided a foot reflector, comprising:

a) a triangular frame having a flat base portion, a first side portion and a second side portion, the top of each of said side portions being joined together at an acute angle and the bottom of each of said side portions being joined to opposite ends of said flat base portion;

b) the base portion having means for supporting a first mirror thereon;

c) the first side portion having a leg support thereon;

d) the second side portion having a second mirror and a third mirror rotatably and adjustably attached thereto, said second mirror attached in the lower portion of said frame and said third mirror attached in the upper portion of said frame;

e) said second mirror and said third mirror having a back surface containing a magnifying mirror thereon.

As will be seen from the drawings, the foot reflector can include grab handles on the first side portion. The triangular frame of the foot reflector includes angle levers for adjusting one or both of said second and said third mirrors. The foot reflector preferable has means such as a ratchet and pawl or other similar means for keeping the second and third mirrors are rotatably attached to the second side portion yet allowing for releasable holding each of said mirrors in a fixed position so that the person examining her foot can keep the mirrors in a desired position while conducting the examination of the foot.

DETAILED DESCRIPTION OF THE PERFERED EMBODIMENTS

Figure 1:
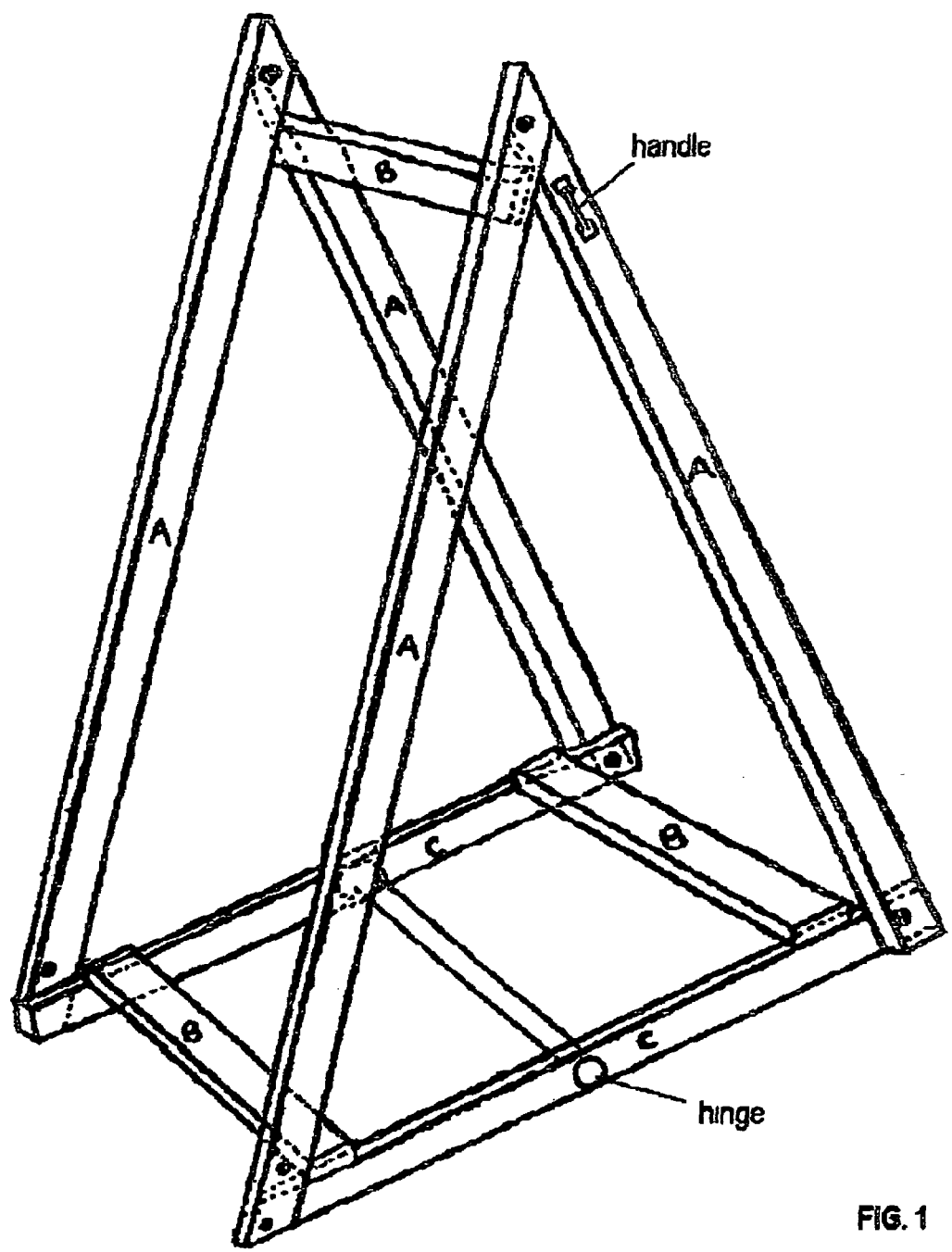
FIG. 1 is a perspective view of the frame, including the handle and the hinge with broken lines superimposed.
Figure 2:
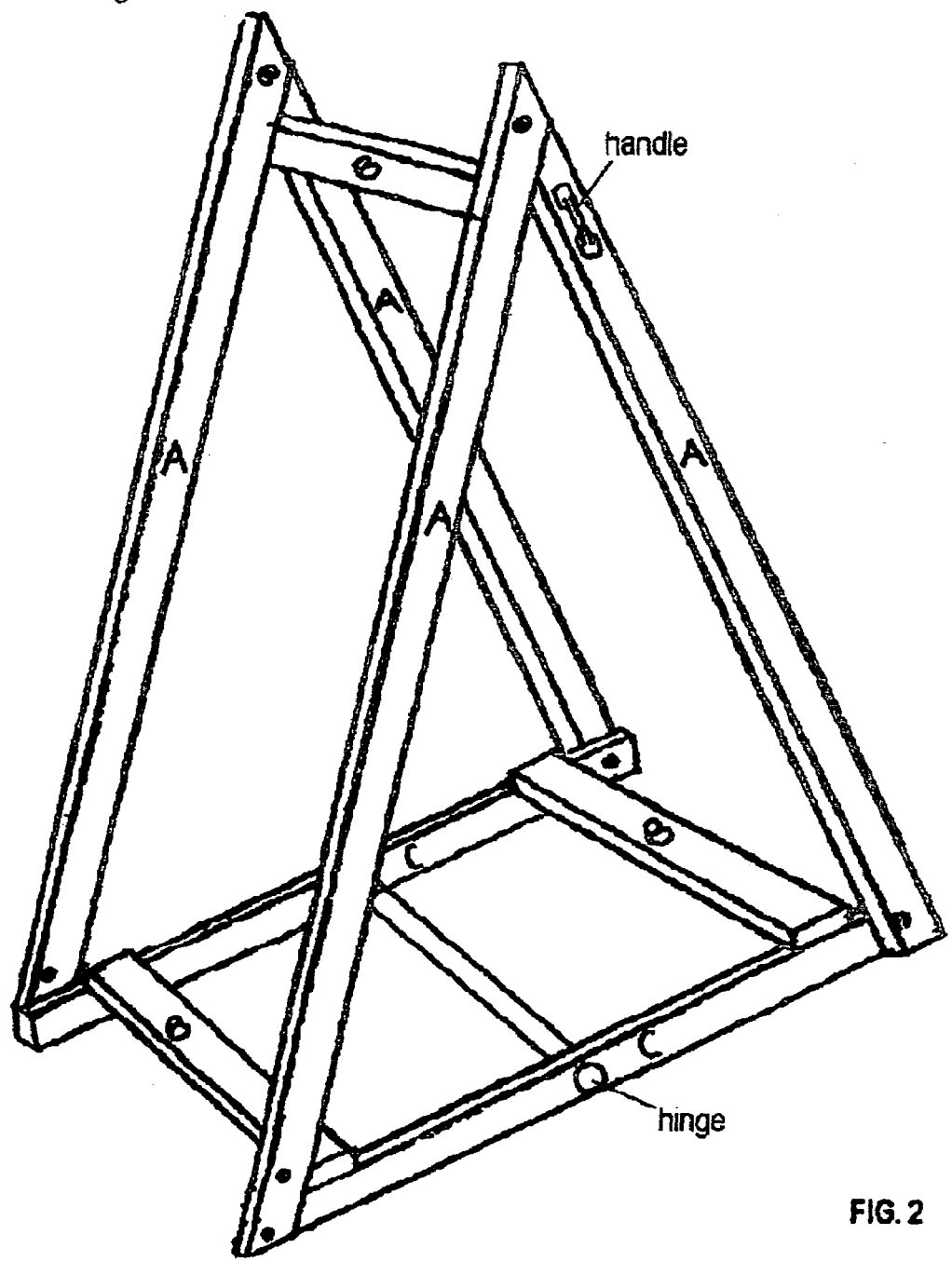
FIG. 2 is a perspective view of the frame, including the handle and the hinge.

FIGS. 1 and 2 is a perspective view of the device's frame. Note that on both lower supports C there is located a connected hinge, which allows the invention to fold for easier storage. The frame may be built of either wood or high strength plastic. The handles, hinges, and fastening devices are all metal and of commercial grade quality. In one preferred aspect of the invention, the overall height of the device is 35 inches, the width is 14½ inches, and the length of the base is 23 inches. It will be understood, however, that the height, width and length of the devise is a matter of choice and that the invention is not dependent upon any specific measurements for any dimension.

Figure 3:
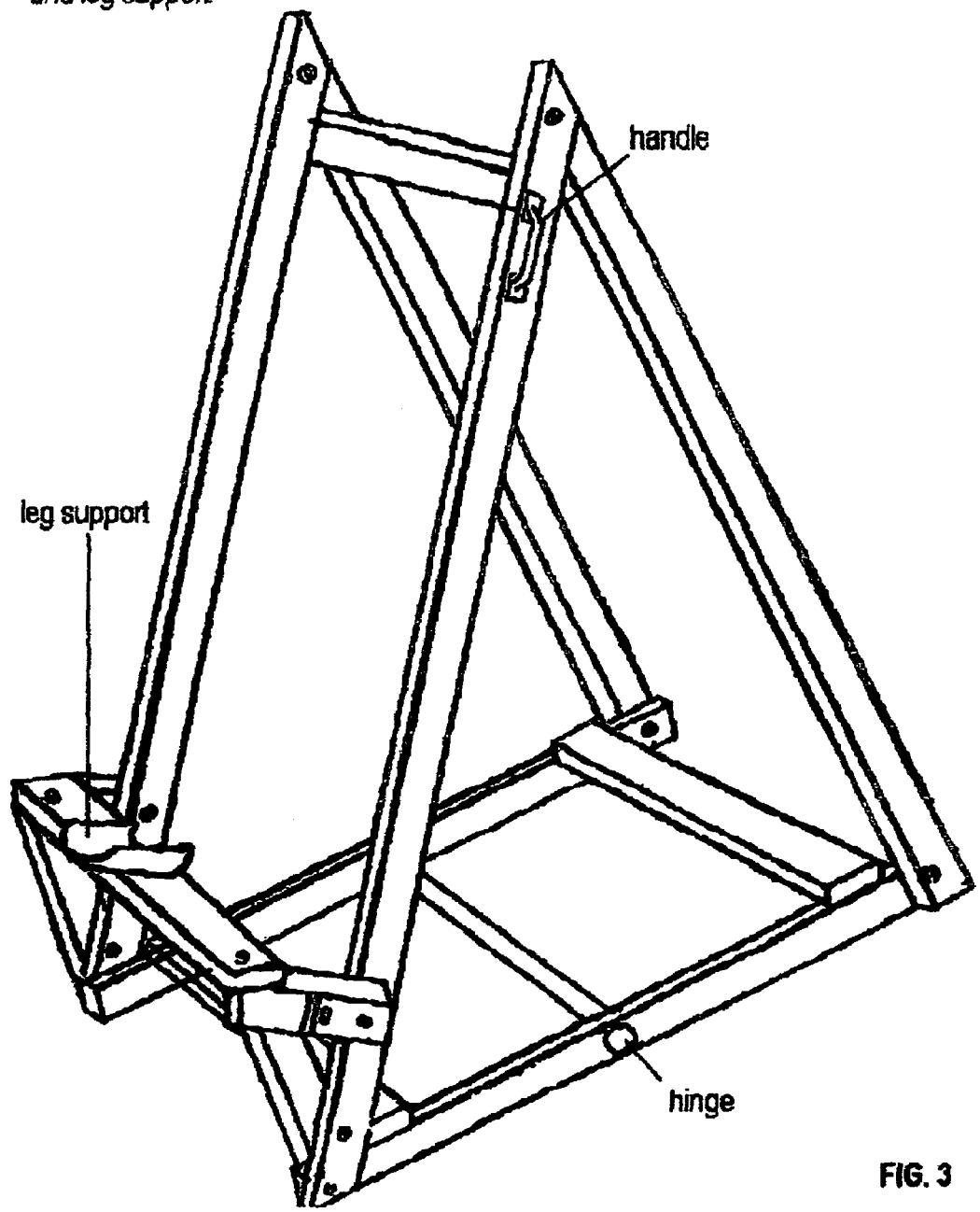
FIG. 3 is a perspective view of the frame, including the handle, hinge, and leg support.
Figure 4:
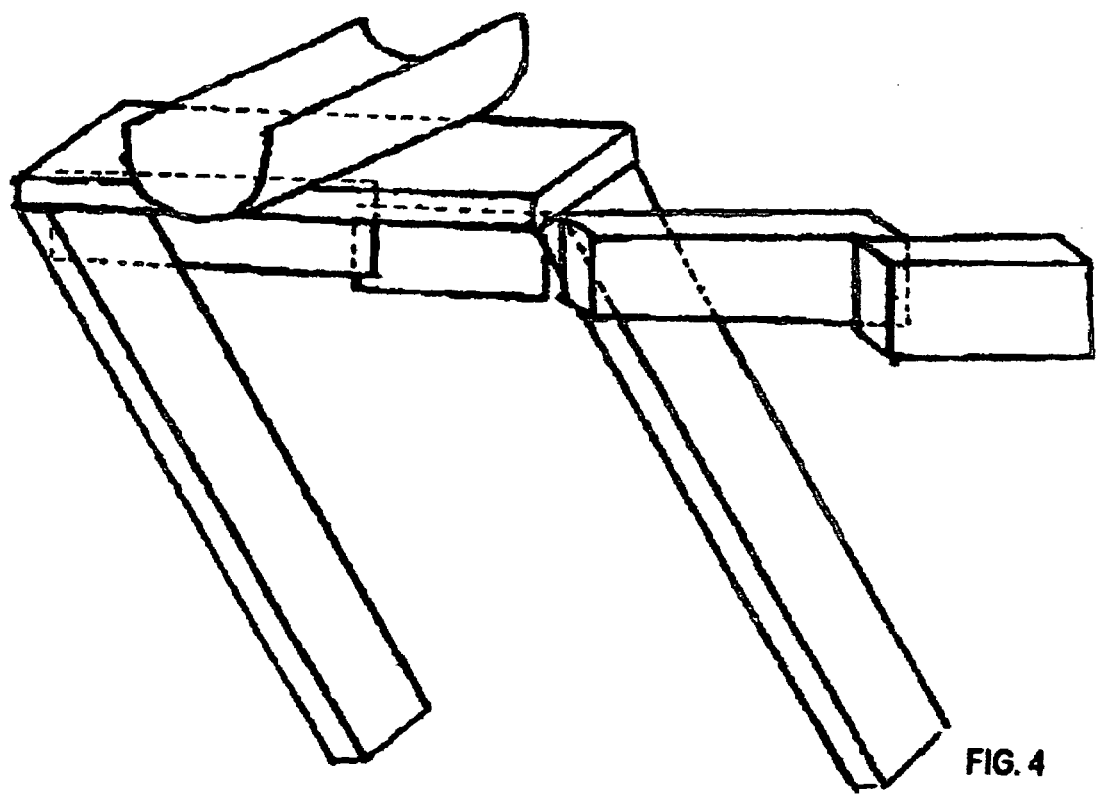
FIG. 4 is a perspective view of the leg support with broken lines superimposed.
Figure 5:
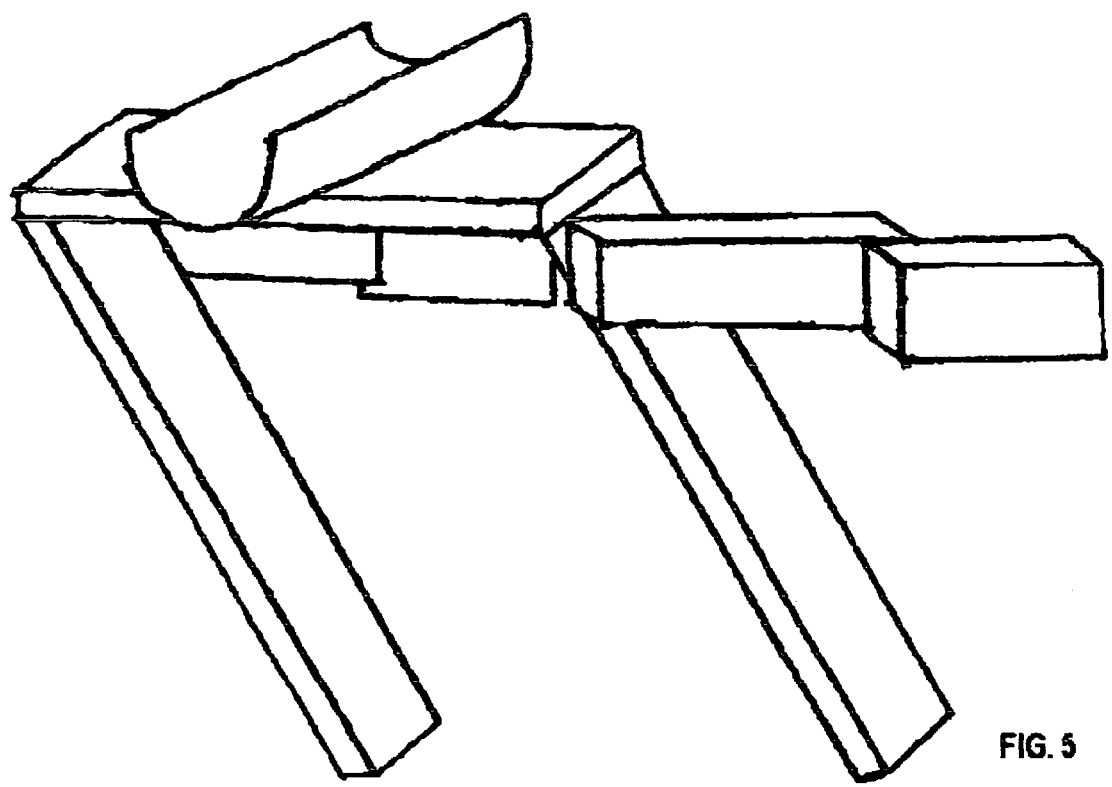
FIG. 5 is a perspective view of the leg support.

FIGS. 3, 4, and 5 contains the inventions frame plus the leg support with its attached framing structure. The framing materials and fasteners are the same as in FIGS. 1 and 2. The leg rest is made out of factory curved, high density, and smooth plastic which can be any suitable thickness, such as about ¼ inch thick. The leg rest is designed so that it has an opening that is wide and long enough, (such as about three inches across, and six inches long) where one places their calf during self-examination. The leg rest is attached to the frame such as with recess screws. The tops can be sealed with paint. The leg rest can also be painted high glass white for ease of cleanliness, if desired.

Figure 6:
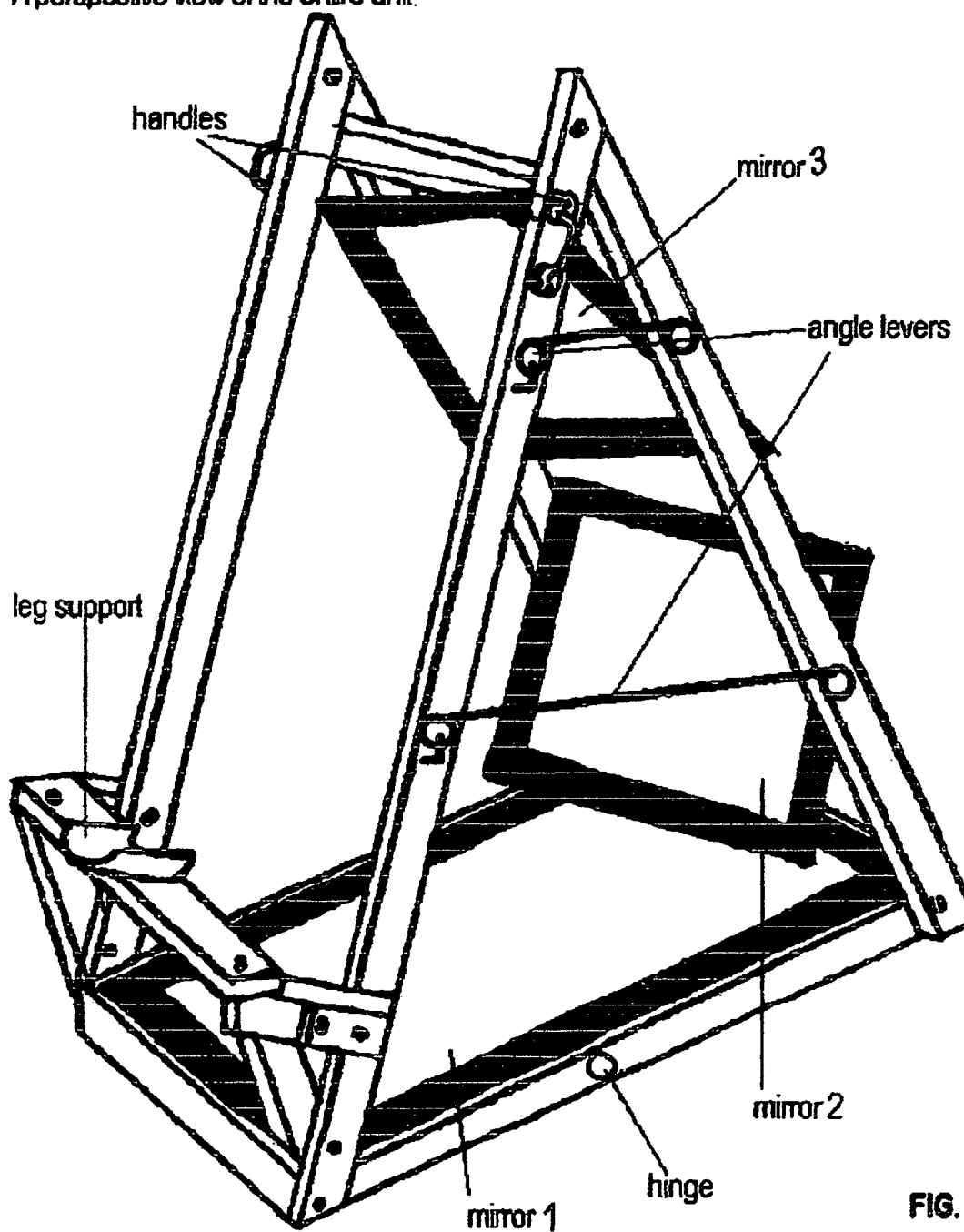
FIG. 6 is a perspective view of the entire unit.

FIG. 6 is a perspective view from the front of the device. This is what the user of the device would observe when being seated in front of the device. For self-examination, one would sit in front of the device and remove any foot covering that they may be wearing. This includes but is not limited to socks, shoes, slippers, or sneakers. One would now place their calf on the leg rest. Then adjust mirrors 2 and 3, using the angle levers, so that mirror 2 reflects the bottom and lower sides of their foot and that mirror three reflects the toes and all the spaces between them. They look for any problems on their foot and write down what they observe. Then they take their calf off of the leg rest, put foot covering back on, get off the chair, and leave.

Following self-examination of both feet, if anything out of the ordinary was observed one should seek the help of a health care professional.

Figure 7:
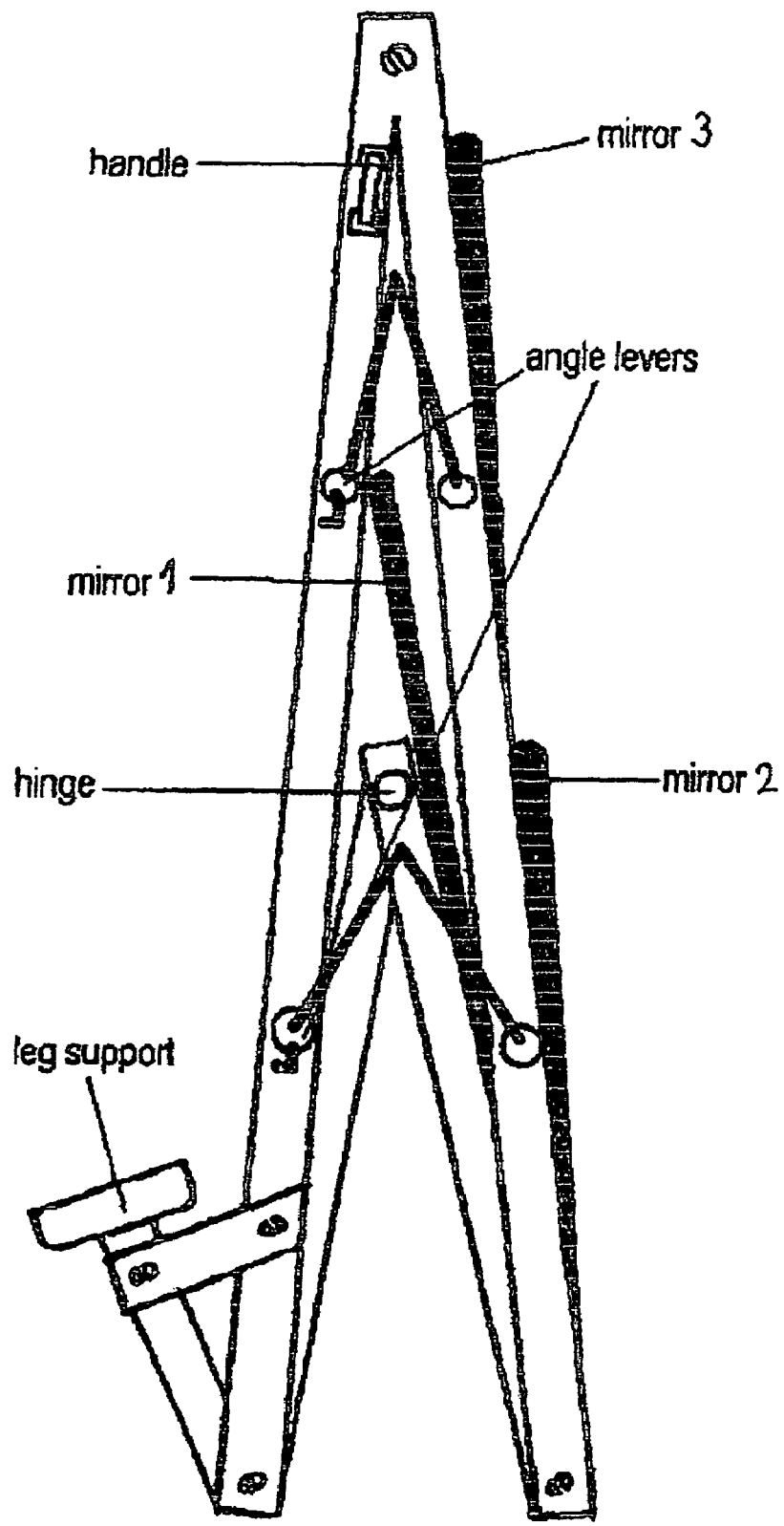
FIG. 7 is a side view of the entire unit in the closed position.

FIG. 7 is a side view of the entire unit in the closed position. Please note that the angle levers and base support C are hinged. Pushing up at the hinge point of supports C and the middle of each angle lever closes the device.

Figure 8:
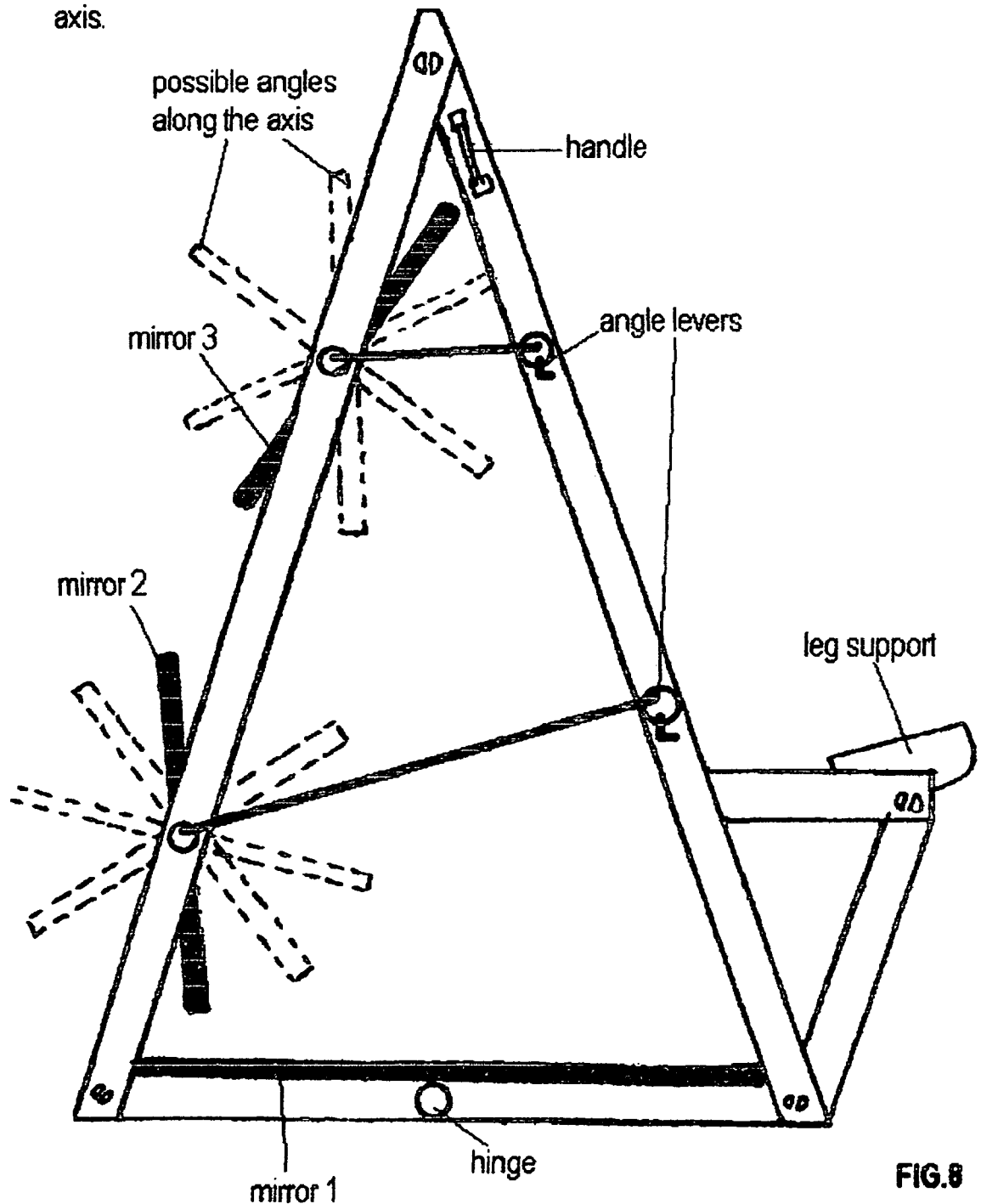
FIG. 8 is a side view of the entire unit in the closed position showing different angles along the rotational axis.

FIG. 8 is a side view of the entire unit with the broken lines representing only some of the many different functional positions of mirrors 2 and 3. Rotation of 360 degrees for mirrors 2 and 3 is necessary because of the fact that they are two sided mirrors. One side of each mirror 2 and 3 has a non-magnification. This is considered a normal mirror. The reverse side of mirrors 2 and 3 are magnification mirrors, with a power of five times normal vision.

Figure 9:
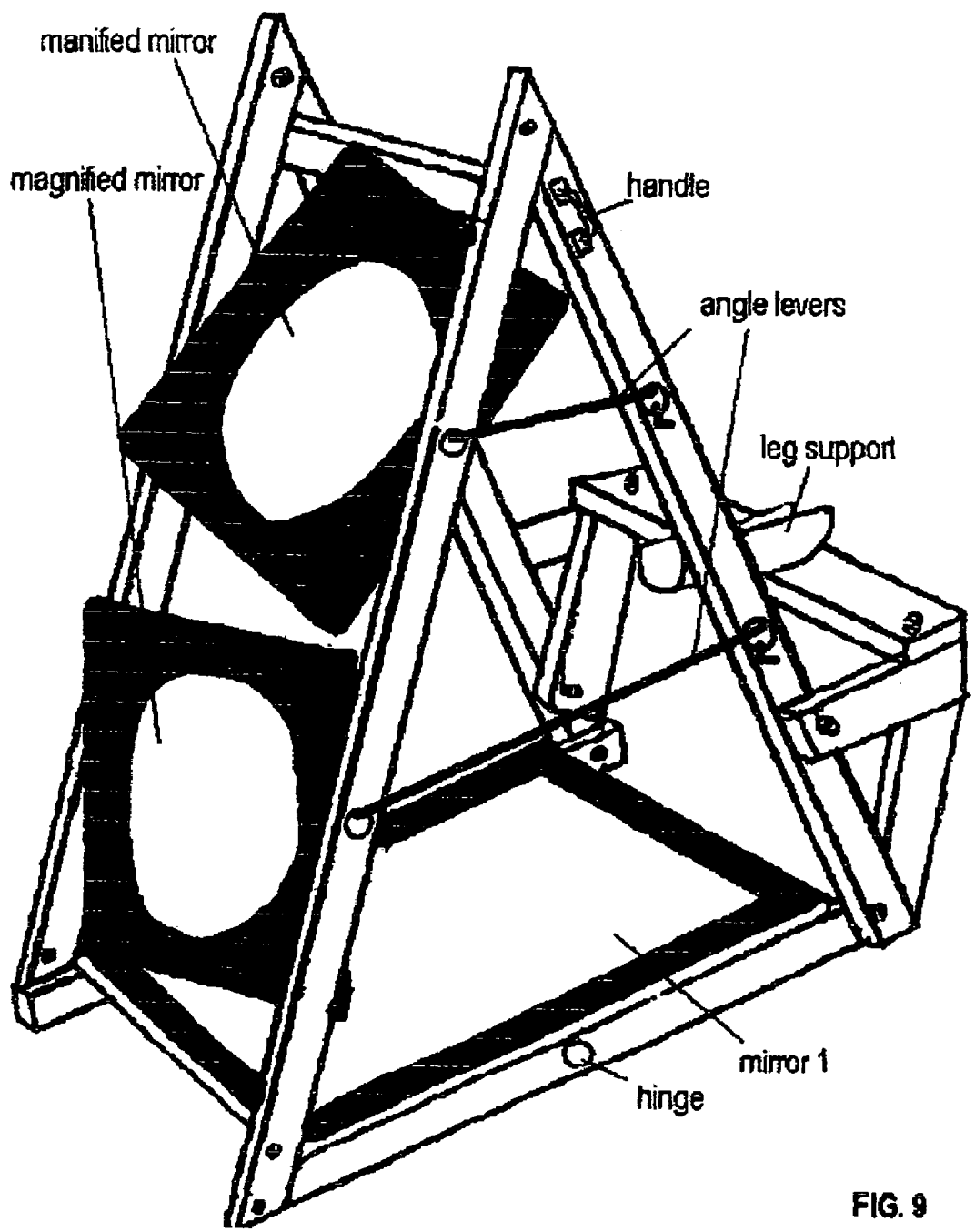
FIG. 9 is a perspective view of the entire unit from the back showing the round magnification mirrors at the rear. They are mirrors 2 and 3.

FIG. 9 is a perspective view of the entire unit from the back of the device. The purpose of this representation is to draw attention to the two magnifying mirrors. They both are glued to the back of mirrors 2 and 3. These magnification mirrors are normally used by people with weak vision or when someone may be trying to look at a very small foreign object, such as a splinter in their foot.

FIG. 9 has mirror 1 as one of the components represented in it. The function of mirror 1 is of two fold. One function is, one may observe various parts of one's foot in mirror 1 directly. The second function is that it performs as a reflective base for mirrors 2 and 3.

FIGS. 6, 7, 8, and 9 allows one to observe the simplicity of the invention. It requires only cleaning of the mirrors and the leg rest for complete functionality. This simplicity leads to lower manufacturing cost and therefore lower cost to the consumer.

FIGS. 6, 7, 8, and 9 allows one to observe how simple it is for the individual to give ones self a complete foot self-examination.

Taking into consideration the ease of maintenance, the relative low cost to the consumer, and the simplicity of use by its design coupled with the fact that all health care professionals who observed its use recommend it. That all testers of the device were pleased with their self-examinations make this invention a must in the homes of people with circulatory problems.

Some of the more important features of the invention include:

1. The Foot Reflector . . . for Your Health is a unique combination of five mirrors with a leg support. This will allow a user of the device to self-examine the entire area of their foot for infections or foreign objects.
2. The Foot Reflector . . . for Your Health has two magnification mirrors which can be adjusted to whatever angle one may need for self-examination.
3. The Foot Reflector . . . for Your Health has two normal mirrors which can be adjusted to whatever angle one may need for self-examination.
4. The Foot Reflector . . . for Your Health has a stationary mirror which is used for direct observation of one's foot and as a reflective base for the other four mirrors.
5. The Foot Reflector . . . for Your Health has a unique leg support system which allows one to comfortably self-examine one's foot.

The following is a complete list of materials used in the manufacture of a device in accordance with the invention. It is as follows 1) 5 pieces of wood or light weight rigid plastic with the dimensions being, for each piece 6 feet long, 1 inch wide, and ½ inch thick, 2) 40 wood screws 2 inches long and 40 nuts with the appropriate size screws, 3) a pint container of high strength glue, 4) 1 mirror 23 inches by 13 inches which includes the ½ inch thick frame, 5) 2 mirrors 14½ inches by 11½ inches including the ½ thick frame, 6) 2 magnification mirrors that magnify 5 times normal vision—the diameter of each is 9 inches without any attached frame, 7) half of a white plastic drain pipe, 6 inches long, 3 inches across, and ¼ inch thick, 8) 1 quart of high gloss white paint, 9) 2 handles each 3 inches long, 10) 2 light weight, centrally hinged rods with a ¼ inch diameter and a 20 inch length, 11) 2 hinges which are 4 inches long for attachment to the middle of each 23 inch long bases C, 12) 2 small curved hooks that can be screwed into the side of the device.

This is the procedure for making a device in accordance with this invention. There are two things that should be noted before beginning. One is that where the word wood is used plastic may be substituted and the other is that the builder, at their discretion, may use just a screw or a bolt and screw assembly. Assembly should be preformed in the following sequence.

1. Center and glue a magnification mirror to the back of each mirror, which measures 14½ inches by 11½ inches.
2. Take two 6 feet long pieces of wood and cut them in half.
3. Take another 6 feet long piece of wood and cut it into two pieces, each piece 23-inches long.
4. Get another piece of wood (6 feet long) and cut it into 3 pieces, each piece 13 inches in length.
5. Drill holes ½ inch from each end of the four 3 feet long and the two 23-inch long pieces of wood.
6. Form a V shape with two of the 3 feet long pieces of wood so that the end hole of one lies over the end hole of the other.
7. Cut each 23 inch long piece in the middle and attach hinges so that they can be folded into an upward position.
8. Lay the hinged 23-inch piece of wood across the bottom of the wide end of the V. Align the drilled holes at each end of the 23-inch pieces of wood with the holes of the V shaped piece and screw together.
9. Repeat above with the remaining set of three feet long pieces of wood and 23-inch long hinged piece of wood.
10. Test both assemblies to make sure that the 23 inch long hinged piece of wood will compress upward and the V opening closes as illustrated as in FIG. 7.
11. As you continue the assembly please refer to FIGS. 1, 2, and 3. These illustrations will make it easier for one to assemble the device.
12. Lay one triangle down so that the base is on the bottom and the apex points in the opposite direction.
13. Stand the 13-inch long piece of wood on the other side of the base. Glue it onto the frame.
14. Repeat with the other 13-inch long piece of wood on the other leg of the triangle.
15. Place the second triangle parallel to the first so that each 13-inch piece of wood sits on the 23-inch base.
16. Glue the 13-inch piece of wood to the base of the $2^{nd}$ bridge so the 13-inch pieces of wood are above the bridge.
17. Place this 13-inch piece of wood parallel to the third 13-inch piece of wood.
18. Attach the two handles approximately one inch from the top of the device with screws.
19. Position mirror 1 on the base, refer to FIG. 6, and attach it with 2 screws and glue. Do this only along the shorter edge, which is opposite the leg support. This will allow the mirror to move freely when one wants to place the device in the closed position, such as in FIG. 7.
20. Position mirror 2 as shown in FIGS. 6, 8, and 9. Attach it to the frame with a single screw on each side. This location is in the middle of the 14½ inch long side of mirror 2. These two attachment screws should each be 11 inches from the bottom of support A. Double check your work by referring to FIG. 8. Make sure the mirror can be rotated 360 degrees. The reason for this is that one side of mirror 2 has normal reflective power and its reverse side has magnification of five times normal.
21. Repeat procedure 20, for mirror 3, with the only difference being that the frame attachment screws will be located 10 inches from the top of support A.
22. Assemble the leg support using FIGS. 4 and 5 as your guide. All attachments should be done with both screws and glue.

23. Using FIG. 6 as your guide, attach the leg support component of the device to the frame opposite of mirror 2.
24. The bottom edge of the curve of the leg support should be 13½ inches from the floor, at the most distant point from mirror 2 while at its opposite edge, which is closest to mirror 2, its height from the floor should be 12½ inches.
25. Attach hooks at the location on the sides of the device, where the angle levers will be located as per FIG. 8.
26. Holes should be drilled large enough on the angle levers so that they can be easily placed on the pictured hook and the protruding screw.
27. The at home user of the device can easily cut the length of the angle levers to a size which is most comfortable for their personal use.

What is claimed is:

1. A foot reflector, comprising:
 a) a triangular frame having a flat base portion, a first side portion and a second side portion, the top of each of said side portions being joined together at an acute angle and the bottom of each of said side portions being joined to opposite ends of said flat base portion;
 b) the base portion having means for supporting a first mirror thereon;
 c) the first side portion having a leg support thereon;
 d) the second side portion having a second mirror and a third mirror rotatably and adjustably attached thereto, said second mirror attached in the lower portion of said frame and said third mirror attached in the upper portion of said frame;
 e) said second mirror and said third mirror having a back surface containing a magnifying mirror thereon.

2. The foot reflector of claim 1, wherein said first side portion includes grab handles thereon.

3. The foot reflector of claim 1, wherein said triangular frame includes an angle lever for adjusting one of said second and said third mirrors.

4. The foot reflector of claim 3, wherein said triangular frame includes a first angle lever for adjusting said second mirror and a second angle lever for adjusting said third mirror.

5. The foot reflector of claim 1, wherein said second and said third mirror are rotatably attached to said second side portion with means for releasable holding each of said mirrors in a fixed position.

6. The foot reflector of claim 1, wherein said base portion is capable of folding upwardly toward the apex of said triangular frame.

* * * * *